US009668971B2

(12) United States Patent
Laza-Knoerr et al.

(10) Patent No.: US 9,668,971 B2
(45) Date of Patent: Jun. 6, 2017

(54) IMMEDIATE-RELEASE BOLUS

(71) Applicant: HY-NUTRITION, Dinard (FR)

(72) Inventors: Anca L. Laza-Knoerr, Saint-Malo (FR); Julien Bonte, Plouer sur Rance (FR)

(73) Assignee: HY-NUTRITION, Dinard (FR)

( * ) Notice: Subject to any disclaimer, the term of this patent is extended or adjusted under 35 U.S.C. 154(b) by 6 days.

(21) Appl. No.: 14/838,668

(22) Filed: Aug. 28, 2015

(65) Prior Publication Data

US 2016/0058700 A1    Mar. 3, 2016

(30) Foreign Application Priority Data

Aug. 29, 2014  (FR) .................................. 14 01933

(51) Int. Cl.
| *A61K 9/00* | (2006.01) |
| *A61K 9/20* | (2006.01) |
| *A61K 33/14* | (2006.01) |
| *A61K 9/46* | (2006.01) |

(52) U.S. Cl.
CPC .......... *A61K 9/0068* (2013.01); *A61K 9/0007* (2013.01); *A61K 9/2009* (2013.01); *A61K 9/2013* (2013.01); *A61K 9/2095* (2013.01); *A61K 33/14* (2013.01)

(58) Field of Classification Search
None
See application file for complete search history.

(56) References Cited

U.S. PATENT DOCUMENTS

| 5,393,535 A * | 2/1995 | Kjems ................... A61K 33/06 424/438 |
| 5,631,289 A * | 5/1997 | Abele ................... A61K 31/19 514/557 |
| 5,962,048 A * | 10/1999 | Register ................. A61K 33/14 426/72 |
| 2007/0190116 A1* | 8/2007 | Lee ...................... A61K 9/0068 424/442 |
| 2010/0008865 A1 | 1/2010 | Fayet et al. |
| 2013/0344005 A1* | 12/2013 | Le Jean ............... A61K 31/194 424/44 |

FOREIGN PATENT DOCUMENTS

| BG | 695 | 10/2004 |
| DE | 202004005428 | 6/2004 |
| EP | 1669080 | 6/2006 |
| EP | 2189154 | 5/2010 |
| EP | 2676657 | 12/2013 |
| WO | 2011152810 | 12/2011 |

OTHER PUBLICATIONS

French Search Report issued in the corresponding European Patent Application No. 1401933, dated May 18, 2015 (2 pages).
International search report for International application No. PCT/TR2011/000151, dated Nov. 17, 2011 (3 pages).

* cited by examiner

*Primary Examiner* — Robert A Wax
*Assistant Examiner* — Caralynne Helm
(74) *Attorney, Agent, or Firm* — Hamre, Schumann, Mueller & Larson, P.C.

(57) ABSTRACT

The subject of the invention is a veterinary product or a nutrition product intended in particular for the prevention and treatment of hypocalcaemia in ruminant animals. The product is in the form of a bolus comprising calcium chloride and an effervescent mixture. Advantageously, the bolus enables a high bioavailability of the calcium and does not cause lesions on the digestive tract of the animal.

18 Claims, No Drawings

IMMEDIATE-RELEASE BOLUS

The subject of the invention is a veterinary product or a nutrition product intended in particular for the prevention or treatment of hypocalcaemia in ruminant animals.

PRIOR ART

With regard to the forced administration of active ingredients to ruminant animals, and for reasons of practicality, the use of "bolus" forms is advantageous. The bolus is a solid device placed by the operator beyond the fold of the tongue of the animal, which the latter swallows, placing it by itself in the reticulorumen.

Parturient paresis, also called milk fever, vitular coma or vitular fever, was described for the first time by Eberhard in 1793 under the name "calving fever". It corresponds to peri-partum hypocalcaemia leading to a specific clinical picture. This metabolic disease can lead to the death of the animal in 12 to 24 hours.

In high producing cows, the beginning of lactation poses a major problem in terms of calcium metabolism. The rapid increase in lactation as soon as calving takes place rapidly increases calcium requirements. The cow, which is coming out of gestation, is not used to releasing its body calcium stores, and a few days are necessary for the mechanisms of this storage release to be set up. A critical period therefore ensues, just after calving, during which the cow which has just calved struggles to maintain its blood calcium at a satisfactory level of about 80 mg/l.

When the blood calcium level drops between 55 and 75 mg/l, generally one hour after calving, the cow enters into subclinical hypocalcaemia (or stage 1 hypocalcaemia), which has few symptoms, but which is known to impair milk production performance levels. Ten to twelve hours later, the blood calcium level can further descend between 30 and 65 mg/l, to below 50 mg/l, and the cow is no longer steady on its feet and lies down. If nothing is done, vital prognosis becomes an issue. The cow is then in stage 2 of vitular fever. Under 30 mg/l (stage 3 hypocalcaemia), the animal goes into a coma and it dies 10 to 24 hours after the appearance of the first signs of dysorexia, usually because of respiratory muscle paralysis.

Vitular fever is generally treated by intravenous injection of calcium in order to very rapidly restore a sufficient blood calcium level. However, this curative procedure falls within the competence of veterinary medicine. It has thus been sought to develop oral calcium supplements which can be given by the farmer.

The digestive system of ruminant animals has the particularity of comprising an enormous reservoir called the reticulorumen, stratified into three phases of different consistency: a gas phase above a solid phase which itself floats above a liquid phase. Only the liquid phase, loaded with microparticles, passes into the rest of the digestive tract.

A solid food resides in the reticulorumen for a longer period of time than a liquid and its absorption into the bloodstream is consequently slower. Conversely, an active ingredient dispensed in liquid form comes into contact with the animal's bloodstream faster, either by means of absorption by the ruminal wall, or by means of a faster passage for the purposes of absorption in the subsequent parts of the digestive tract.

The first calcium-based nutritional supplements were provided in the form of a gel for this reason. The gel, which contains calcium chloride, must be administered with slow swallowing and the animal must have its head raised. Moreover, the gel causes burning in the oesophagus and has a very unpleasant taste, which requires the animal to be restrained throughout swallowing. In reality, the farmer does not always adhere to these dispensing recommendations and false swallowing ensues, with serious and painful pulmonary consequences for the animal.

In order to overcome these drawbacks, solid products such as the bolus have been proposed, since they are administered much more rapidly (in approximately one minute) and without risk of false swallowing. One of these products, sold under the brand name Bovikalc®, provides calcium in the form of calcium chloride. This bolus also contains an excipient in the form of calcium sulphate which is not metabolized and which forms a viscous paste in the rumen. As it happens, hypocalcaemia can cause a loss of ruminal motricity, which is, however, essential for stirring the food mass, facilitating bacterial inoculation, regurgitating foods, eliminating fermentation gases and controlling discharge of the content to the distal portions of the digestive tract. Thus, calcium sulphate can reduce the assimilation of calcium chloride, if the animal is at an advanced clinical stage of hypocalcaemia. It would therefore be desirable to have available a calcium chloride-based product which is very fluid in the rumen and promotes calcium dispersion throughout its volume.

In addition, according to the teaching of document U.S. Pat. No. 5,395,622, it is necessary to add calcium sulphate and water to calcium chloride in order to obtain a paste of sufficient viscosity, the calcium chloride dose of which can be controlled. Calcium sulphate is therefore required for the production of a solid product containing calcium chloride.

Calcium chloride is a calcium salt which is highly soluble in water and which has a very good bioavailability. Consequently, it is preferred to use this salt for the treatment of ruminants suffering from vitular fever, the clinical condition of which may abruptly worsen. Nevertheless, the prior art products containing calcium chloride are aggressive for the mucosae and their administration causes lesions on the digestive tract of the animal.

Consequently, it has been proposed, in application FR 2 992 219, to replace calcium chloride with a mixture of calcium formate and calcium carbonate.

Given the prior art, there therefore still remains a need to provide a calcium provision which simultaneously is easy to administer, is easy to produce, contains a high dose of calcium, has a high bioavailability, and preserves the integrity of the digestive tract of the animal.

It has been discovered, in the context of the present invention, that it is possible, against all expectations, to provide a product comprising calcium chloride which remedies the prior art drawbacks.

DESCRIPTION OF THE INVENTION

The subject of the invention is an immediate-release bolus which can be in the form of an anhydrous tablet of powders comprising from 10% to 50% by weight of calcium. This bolus is prepared from calcium chloride and from the combination of an acidic compound and a basic compound capable of generating gas release in an aqueous medium. This combination is advantageously in an amount sufficient to enable the dissolution of the calcium chloride in the rumen of the animal without causing any lesion.

For the purposes of the invention, a bolus is a solid product intended to be administered to an animal orally, dry, that is to say without having been predissolved in water. The bolus dissolves and becomes effervescent in the ruminal fluid, after having been administered dry. The bolus of the invention is advantageously a tablet of powders, in which the calcium chloride, the basic compound and the acidic compound are homogeneously distributed throughout the mass of the bolus.

The bolus of the invention is preferably anhydrous. The term "anhydrous product" is intended to mean a product which does not contain, or contains less than 0.5% by weight of water which is not bonded to other compounds by chemical bonds, for example water which is not in the form of a hydrate. Thus, the anhydrous bolus of the invention may contain water in the form of hydrates, also called crystallization water.

After administration, the tablet begins to dissolve in the ruminal fluid, the pH of which is generally between 5.5 and 7. The acidic compound reacts with the basic compound and generates a release of gas which accelerates the dispersion and solubilization of the calcium chloride over the entire surface of the rumen. The inventors have discovered that the formation of a certain amount of gas makes it possible to increase the area of contact between the ruminal fluid and the calcium salt by dispersing it, while at the same time remaining harmless to the animal. They have also discovered that, in this tablet, the calcium chloride does not cause inflammation of the mucosae of the stomach and of the rumen, or necrotic lesions of the abomasum.

The bolus of the invention can be used as a food supplement in a method for feeding ruminants. The bolus may also be used for the treatment or prevention of hypocalcaemia in a ruminant animal.

More specifically, the invention relates to an anhydrous bolus in the form of a solid tablet of powders comprising 10% to 50% by weight of calcium, characterized in that it is obtained by mixing calcium chloride and a sufficient amount of an acidic compound and of a basic compound capable of generating release of gas in an aqueous medium, the three compounds being in the form of powders.

The term "basic compound" is intended to mean a compound which converts into a salt in an aqueous medium by capture of a proton. The term "acidic compound" is intended to mean a compound which converts into a salt in an aqueous medium by loss of a proton.

The bolus of the invention is preferably an immediate-release product in the sense that the active ingredient that it carries, in this case calcium, reaches a maximum plasma concentration less than one hour, preferably less than 45 minutes, more preferably less than 30 minutes, after its oral administration to a ruminant.

The bolus of the invention is preferably an immediate-release product in the sense that 100 grammes of the bolus according to the invention has the advantage of completely dissolving in two liters of water at pH=7, at a temperature of 38° C. in less than one hour, preferably between 25 and 35 minutes.

The calcium chloride may correspond to the formula $CaCl_2.xH_2O$, with x ranging from 0 to 6. The value of x is, for example, equal to 0, 1, 2, 4 or 6. The calcium chloride may be anhydrous calcium chloride, calcium chloride dihydrate, calcium chloride tetrahydrate or calcium chloride hexahydrate. In one embodiment of the invention, the calcium chloride is calcium chloride dihydrate (x=2).

The calcium chloride is preferably anhydrous. The proportion of the calcium chloride in the bolus is preferably between 10% and 50% by weight of the weight of the bolus, the calcium chloride possibly being in hydrate form. The calcium chloride dihydrate represents, for example, between 35% and 55% by weight of the weight of the bolus, preferably between 40% and 50% by weight.

The bolus of the invention may contain, in addition to the calcium chloride, calcium salts or calcium chelates with amino acids. An organic or inorganic calcium salt may be chosen from the group consisting of calcium gluconate, calcium formate, calcium propionate, calcium citrate, calcium carbonate, calcium stearate, calcium pidolate and calcium iodate (also called lautarite) $Ca(IO_3)_2$.

The bolus preferably contains less than 25% by weight of calcium sulphate, even more preferably less than 5% by weight of calcium sulphate. It is preferably free of calcium sulphate. The bolus may contain less than 5% by weight of calcium carbonate and less than 5% by weight of calcium formate. It is possible for the bolus not to contain calcium formate.

The bolus is advantageously not coated in a protective film at the time of its administration, as is the case with the calcium chloride-based products known to those skilled in the art.

The weight of the bolus is generally between 40 and 200 g, for example equal to 60 g, 70 g or 100 g. The hardness of the bolus may be between 1 and 15 kPa, for example may be equal to 6, 9 or 13 kPa according to its size.

The bolus preferably contains between 10 g and 50 g of calcium (Ca) per 100 g of bolus, more preferably between 12 and 20 g of calcium/100 g of bolus, which can represent a content of between 45% and 70% by weight of calcium-containing compounds required to prepare the product.

According to one embodiment, the bolus comprises an inorganic or organic acidic compound and an inorganic or organic basic compound so that the bolus becomes effervescent once it comes into contact with the reticuloruminal fluid after it has been administered.

An effervescent pair capable of generating carbon dioxide in the rumen of the animal comprises at least one solid acidic compound and at least one solid basic compound.

The acidic compound preferably represents from 7% to 15% by weight of the weight of the bolus.

The solid acidic compound can be chosen from the group consisting of organic acids, organic acid anhydrides, and alkaline metal salts of organic acids. Organic acids are, for example, malic acid, fumaric acid, tartaric acid, itaconic acid, maleic acid, citric acid, adipic acid, succinic acid or esaconic acid. An organic acid anhydride is, for example, itaconic anhydride. Alkaline metal salts of organic acids are, for example, chosen from the group consisting of monosodium citrate, potassium acid tartrate and potassium bitartrate.

The solid acidic compound is preferably in anhydrous form. The acid may be in the group consisting of inorganic acids, such as sulfamic acid or phosphoric acid, and inorganic acid salts.

The solid basic compound may be an alkali or alkaline-earth metal oxide or hydroxide. The basic compound may also be a carbonate salt ($CO_3^{2-}$) or a bicarbonate salt ($HCO_3^-$). The basic compound may be chosen from the group consisting of calcium oxide, alkaline metal carbonates, alkaline metal bicarbonates, alkaline-earth metal carbonates and alkaline-earth metal bicarbonates.

The basic compound represents, for example, from 2% to 35%, preferably from 5% to 30% by weight, of the weight of the bolus.

The solid basic compound is, for example, chosen from the group consisting of lithium carbonate, sodium carbonate, potassium carbonate, magnesium carbonate, calcium carbonate, lithium bicarbonate, sodium bicarbonate, potassium bicarbonate, magnesium bicarbonate and calcium bicarbonate.

The solid basic compound may also be ammonium carbonate or ammonium bicarbonate.

For example, citric acid is chosen as acidic compound and sodium bicarbonate is chosen as basic compound. Calcium carbonate may also be chosen as basic compound: in this case, the bolus contains an amount of calcium carbonate required to generate the release of gas, and an amount of calcium carbonate which does not contribute to the effervescence reaction and that is assimilated by the ruminant in the form of a calcium ion. In this embodiment, the bolus of the invention preferably contains between 2% and 35% by weight of calcium carbonate relative to the weight of the bolus, for example from 5% to 30%.

The acidic compound and the basic compound are preferably in equivalent molar proportions for producing carbon dioxide.

Anhydrous citric acid is preferably used as acidic compound, since citric acid can react with calcium carbonate in the presence of water in the rumen to form calcium citrate, which can be absorbed by the intestines of the animal.

The amounts of organic acid and of calcium carbonate are preferably such that the effervescence reaction takes place in the rumen of the animal for a period of time sufficient to disperse and dissolve the entire amount of calcium chloride contained in the bolus.

The bolus of the invention enables a rapid and significant rise in the calcium blood level. It completely dissolves in less than one hour in the ruminal fluid at 40° C.

The bolus, when it is prepared by compression of powders, advantageously comprises any additive required for the forming thereof, in particular fillers and lubricants required for the compression of the powders in order to obtain a solid form that can be administered in the form of a large tablet. The fillers are generally chosen from sugars, such as lactose or sorbitol. The lubricant is advantageously calcium stearate or magnesium stearate.

The tablet may have the shape of a cylinder with a diameter of between 1 and 5 cm.

The bolus of the invention may also comprise at least one trace element or one vitamin, for example magnesium, magnesium in a form chelated with amino acids, B-group vitamins, such as niacin (B3), folic acid (B9), riboflavin (B2), pantothenic acid (B5) and cobalamin (B12), or vitamin D3 (cholecalciferol).

The bolus of the invention can be obtained by means of a powder compression process comprising the steps of
mixing of the calcium chloride, the basic compound and the anhydrous acidic compound, all three in the form of powders, until a homogenous premix is obtained, and
compression of the premix at a temperature of between 25 and 100° C., and at a pressure of between 1 and 20 kPa.

The process of the invention has the advantage of not using water and of being simpler than the prior art processes making it possible to dose the calcium chloride.

The powder compression process may be direct or by granulation. The three compounds are preferably in the form of anhydrous powders. Preferably, more than 50% by weight—preferably more than 55% by weight—of the ingredients used to produce the bolus are anhydrous powders, the particle size of which is less than 5 mm, more preferably 2 mm.

The particle size can be measured by any method known to those skilled in the art, for example by laser diffraction. ISO standard 13320-2009 describes one of these methods.

The average sizes of the particles of a powder are calculated from the plot of the particle size curve according to statistical analyses of the population of particles by weight or by volume. The diameter $D_x$ is defined as the diameter such that x % by volume or by weight of the population consists of particles of size smaller than x.

More than 50% by weight of the powders used to produce the tablet of the invention preferably have a $D_{90}$ of less than 3 mm, more preferably a $D_{90}$ of less than 2 mm.

The calcium chloride is a powder preferably having a $D_{90}$ of less than 1.5 mm and a $D_{50}$ of less than 0.5 mm. The particle size of the calcium chloride is, for example, such that $D_{100}$ is less than 2 mm, $D_{65}$ is less than 1 mm and $D_{50}$ is less than 0.5 mm.

The powdered basic compound preferably has a particle size of between 0.1 and 0.5 mm. For example, a basic compound is chosen such that $D_{85}$ is less than 0.5 mm and $D_{15}$ is greater than 0.1 mm.

The compression force applied is preferably between 1 and 15 kPa. The compression force applied may be less than or equal to 10 kPa, thereby increasing the rate of dissolution of the bolus in an aqueous medium.

A subject of the invention is also the bolus which has just been described above, for use thereof in the treatment or prevention of hypocalcaemia in ruminant animals.

For the purposes of the invention, hypocalcaemia is not necessarily a metabolic disorder. Its prevention does not systematically come under the prevention of a disease. Hypocalcaemia for the purposes of the invention is a blood calcium level less than or equal to 80 mg/l.

The ruminant animals are, for example, cattle, members of the sheep family, members of the goat family or buffalo, more preferably females exhibiting increased calcium requirements, in particular females undergoing lactation, for example dairy cows.

The bolus of the invention is of quite particular interest in treatment for preventing hypocalcaemia in female cattle before calving or at the beginning of lactation, and in particular for preventing vitular fever. For the purposes of the invention, vitular fever is a metabolic disorder which occurs around the time dairy cows drop their young.

The bolus is preferably administered before calving, as soon as the signs indicating calving occur, or during calving by the cow. This provision restores the blood calcium level and maintains it above the critical threshold, preferably above 80 mg/l, thus reducing the risk of vitular fever. The bolus is preferably administered before any clinical sign of hypocalcaemia or before any drop in blood calcium level, in order to avoid any subsequent additional treatment, and in particular calcium gluconate infusions.

In one embodiment, a second bolus is administered at least 12 hours after the first.

An administration 2 to 3 days before calving enables a sufficient increase in blood calcium level to avoid any risk of vitular fever.

The supplementation may be carried out three times: 10 to 15 g of calcium 24 hours before calving, 10 to 15 g one to two hours before calving, 10 to 15 g ten to fourteen hours after calving.

The calcium provision is advantageously limited during the three weeks to fifteen days which precede the animal dropping its young. A daily dose may be between 50 and 125 g/day. For better response and efficacy in the control of hypocalcaemia, one dose is given at calving and another 24 hours later.

The use of calcium chloride causes, in parallel to the increase in blood calcium level, acidification of the blood since chloride is a strong anion, and its absorption into the blood is rapid and causes a slight decrease in pH in order to maintain blood electroneutrality. The oral administration of calcium chloride may thus induce metabolic acidosis which can lead to a decrease in appetite. The amount of calcium that can be provided without any risk is a maximum of 120 grammes per day.

Moreover, it is important to sequence the calcium intakes in order to avoid a sawtooth blood calcium level, without however multiplying the administration actions by the carer.

A subject of the invention is also a ruminant animal nutrition process comprising the administration of a bolus as previously described.

According to this aspect of the invention, the bolus can promote maintenance of a good general condition in order to support milk production or to increase milk production.

The rapid-calcium-release bolus may be a bolus which dissolves in vitro at 40° C. in ruminal fluid with a pH between 5.5 and 7, in a period of between 5 minutes and 1 hour, for example between 10 and 40 minutes, for example between 25 and 35 minutes.

The characteristics which have been described above in relation to the boluses apply to the administration process of the invention, to the nutrition process, and to the production process of the invention.

The invention is illustrated in greater detail by the following examples.

Example: Immediate-Release Anhydrous Calcium Bolus

Two boluses having the following composition were prepared. The percentages are by weight.

| Ingredients | Bolus of 60 g | Bolus of 100 g |
| --- | --- | --- |
| Calcium chloride ($CaCl_2 \cdot 2H_2O$) | 40.81% | 49.55% |
| Citric acid | 7.00% | 7.00% |
| Calcium carbonate | 30.00% | 10.00% |
| Sorbitol | 11.28% | 29.65% |
| Vitamins and minerals | qs 100% | qs 100% |
| Magnesium stearate | 0.80% | 0.80% |

All the ingredients are introduced into a Robotainer mixer. The mixture of powder, which may or may not be granulated, is subsequently sieved and then compressed in a Froderais 2B tablet pressure at a pressure of 6 kPa (for the 60 g bolus) and of 13 kPa (for the 100 g bolus).

The in vitro tests in ruminal fluid (pH 7) at 38° C. showed complete dissolution of the boluses in 25 to 35 minutes.

The invention claimed is:

1. A method for the treatment or prevention of hypocalcaemia in a ruminant animal in need thereof, comprising placing an anhydrous bolus in a form of a solid tablet beyond a fold of a tongue of the ruminant animal, whereby the ruminant animal swallows the anhydrous bolus so that the anhydrous bolus falls into reticuloruminal fluid in the rumen of the ruminant animal,
wherein said anhydrous bolus comprises a calcium chloride, citric acid and a calcium carbonate or bicarbonate,
wherein the citric acid and the calcium carbonate or bicarbonate
react in the presence of water when the anhydrous bolus comes into contact with the reticuloruminal fluid,
generate carbon dioxide that accelerates dispersion of the calcium chloride over the surface of the rumen to avoid formation of lesions, and
form calcium citrate that is absorbed by intestines of the ruminant animal, and
wherein calcium is present in the bolus in an amount between 10% to 50% by weight of the weight of the bolus.

2. The method of claim 1, wherein the anhydrous bolus contains an amount of calcium carbonate or calcium bicarbonate that is sufficient to generate carbon dioxide, and an amount of calcium carbonate or bicarbonate that does not contribute to carbon dioxide production and is assimilated by the ruminant animal in the form of a calcium ion.

3. The method of claim 1, wherein the calcium chloride is selected from the group consisting of anhydrous calcium chloride, calcium chloride dihydrate, calcium chloride tetrahydrate, calcium chloride hexahydrate, and mixtures thereof.

4. The method of claim 3, wherein the calcium chloride is calcium chloride dihydrate.

5. The method of claim 1, wherein the anhydrous bolus contains between 2% and 35% by weight of calcium carbonate or calcium bicarbonate, between 35% and 55% by weight of calcium chloride dihydrate, and from 7% to 15% by weight of citric acid, the weight percentages being expressed with respect to the weight of the bolus.

6. The method of claim 1, wherein said anhydrous bolus contains less than 25% by weight of calcium sulphate.

7. The method of claim 1, wherein the calcium chloride is in a powder form having a $D_{90}$ of less than 1.5 mm and a $D_{50}$ of less than 0.5 mm.

8. The method of claim 1, wherein the anhydrous bolus further comprises at least one trace element or vitamin selected from the group consisting of magnesium, B-group vitamins selected from the group consisting of niacin (B3), folic acid (B9), riboflavin (B2), pantothenic acid (B5) and cobalamin (B12), and vitamin D3 (cholecalciferol).

9. A method for the treatment or prevention of hypocalcaemia in a ruminant animal in need thereof, said method comprising a step of placing an anhydrous bolus in the form of a solid tablet beyond a fold of a tongue of the ruminant animal, whereby the ruminant animal swallows the anhydrous bolus so that said anhydrous bolus falls into the reticuloruminal fluid in the rumen of the ruminant animal, wherein said anhydrous bolus comprises:
calcium in a content of 10% to 50% by weight of the weight of the bolus,
a calcium chloride, an acidic compound and a basic compound that are in the form of powders, wherein the acidic compound and the basic compound react together and generate gas in the reticuloruminal fluid that accelerates dispersion of the calcium chloride over the surface of the rumen.

10. The method of claim 9, wherein the basic compound is calcium carbonate or calcium bicarbonate that is in a sufficient amount both to generate carbon dioxide and be assimilated in a form of a calcium ion by the ruminant animal.

11. The method of claim 9, wherein the anhydrous bolus contains between 2% and 35% by weight of calcium carbonate or calcium bicarbonate and between 35% and 55% by weight of calcium chloride.

12. The method of claim 9, wherein calcium chloride is selected in the group consisting of anhydrous calcium chloride, calcium chloride dihydrate, calcium chloride tetrahydrate, calcium chloride hexahydrate, and mixtures thereof.

13. The method of claim 12, wherein the calcium chloride is calcium chloride dihydrate.

14. The method of claim 9, wherein carbon dioxide gas is generated and disperses the entire amount of calcium chloride contained in the bolus.

15. The method of claim 9, wherein the calcium chloride is in a form of a powder having a $D_{90}$ of less than 1.5 mm and a $D_{50}$ of less than 0.5 mm.

16. The method of claim 9, wherein the basic compound represents from 2% to 35% by weight of the weight of the bolus.

17. The method of claim 9, wherein the acidic compound represents from 7 to 15% by weight of the weight of the bolus.

18. The method of claim 16, wherein the basic compound is a carbonate salt or a bicarbonate salt.

\* \* \* \* \*